(12) United States Patent
White

(10) Patent No.: US 11,317,933 B1
(45) Date of Patent: May 3, 2022

(54) NASAL CLEANING TOOL

(71) Applicant: Nathedra G. White, New Orleans, LA (US)

(72) Inventor: Nathedra G. White, New Orleans, LA (US)

(*) Notice: Subject to any disclaimer, the term of this patent is extended or adjusted under 35 U.S.C. 154(b) by 79 days.

(21) Appl. No.: 16/153,115

(22) Filed: Oct. 5, 2018

Related U.S. Application Data

(60) Provisional application No. 62/568,376, filed on Oct. 5, 2017.

(51) Int. Cl.
*A61B 17/24* (2006.01)
*B08B 1/00* (2006.01)
*B08B 3/08* (2006.01)
*A61M 31/00* (2006.01)

(52) U.S. Cl.
CPC ............ *A61B 17/24* (2013.01); *A61M 31/00* (2013.01); *B08B 1/005* (2013.01); *B08B 3/08* (2013.01); *A61B 2017/246* (2013.01); *A61B 2217/007* (2013.01); *A61M 2210/0618* (2013.01)

(58) Field of Classification Search
CPC ........ A61K 9/0043; A61B 2018/00327; A61B 17/24; A61B 2017/246; A61M 2210/0618; A61M 31/00; A61M 3/0279; A61F 13/126; A61H 35/04
See application file for complete search history.

(56) References Cited

U.S. PATENT DOCUMENTS

| | | | |
|---|---|---|---|
| 1,381,829 A * | 6/1921 | Hartman | A61F 5/08 606/162 |
| 1,658,801 A * | 2/1928 | Condren | A61B 17/22 606/162 |
| 2,096,162 A * | 10/1937 | Daley | A61B 17/22 606/162 |
| 2,135,052 A | 11/1938 | Rose | |
| 2,811,283 A * | 10/1957 | Bowen | B05B 11/04 222/109 |
| 3,010,454 A * | 11/1961 | Lucie | A61M 3/0216 604/24 |
| 3,363,808 A * | 1/1968 | Gorman | A61M 11/02 222/633 |
| 3,635,218 A | 1/1972 | Ericson | |
| 3,818,911 A * | 6/1974 | Fournier | A61F 13/38 604/1 |
| 3,938,898 A * | 2/1976 | Reitknecht | A61M 35/006 401/183 |
| 4,258,714 A * | 3/1981 | Leopoldi | A61M 3/0262 604/118 |
| 4,513,891 A * | 4/1985 | Hain | A61M 15/08 222/213 |

(Continued)

FOREIGN PATENT DOCUMENTS

WO    WO-2018032102 A1 *  2/2018 .......... A61M 11/008

OTHER PUBLICATIONS

Barrel, Accessed Aug. 17, 2020, Wolfram MathWorld, <https://mathworld.wolfram.com/Barrel.html> (Year: 2020).*

*Primary Examiner* — Scott J Medway

(74) *Attorney, Agent, or Firm* — Cramer Patent & Design, PLLC; Aaron R. Cramer

(57) ABSTRACT

A nasal cleaning tool incorporates a reservoir in fluid communication with a nozzle. Secured to about a distal end of the nozzle is a helical-shaped cleaning head. The reservoir in one (1) embodiment is fashioned as a deformable bulb.

2 Claims, 3 Drawing Sheets

(56) References Cited

U.S. PATENT DOCUMENTS

| | | | | |
|---|---|---|---|---|
| 4,746,238 A * | 5/1988 | Levine | A61F 13/38 | 401/196 |
| 4,925,128 A * | 5/1990 | Brody | B05B 11/047 | 222/211 |
| 5,152,742 A * | 10/1992 | Simpson | A45D 34/042 | 401/132 |
| 5,806,723 A * | 9/1998 | DuBose | B65D 41/265 | 128/203.15 |
| 5,899,878 A * | 5/1999 | Glassman | A61M 3/0216 | 604/48 |
| D432,239 S | 10/2000 | Shimizu | | |
| 6,241,705 B1 * | 6/2001 | Ko-Wen | A61M 3/0241 | 604/73 |
| 6,293,436 B2 * | 9/2001 | Faughnder | B65D 47/061 | 222/211 |
| 6,361,521 B1 * | 3/2002 | Erickson | A61M 3/0262 | 604/37 |
| 6,540,718 B1 * | 4/2003 | Wennek | A61M 3/0241 | 604/94.01 |
| 6,669,059 B2 * | 12/2003 | Mehta | A61H 35/04 | 222/211 |
| 6,688,497 B2 * | 2/2004 | Mehta | A61H 35/04 | 222/211 |
| D489,133 S | 4/2004 | Shimizu | | |
| 6,907,879 B2 * | 6/2005 | Drinan | A61B 5/411 | 128/200.14 |
| D545,431 S | 6/2007 | Khademhosseini | | |
| 7,862,548 B2 * | 1/2011 | Javer | A61H 35/04 | 604/212 |
| 7,951,106 B1 * | 5/2011 | Perez | A61F 11/006 | 604/11 |
| 7,959,597 B2 * | 6/2011 | Baker | A61M 3/0208 | 604/28 |
| 7,971,761 B1 * | 7/2011 | Kudlu | A61M 3/0208 | 222/481.5 |
| 8,241,236 B2 * | 8/2012 | Yardley | A61B 17/24 | 604/2 |
| 8,409,152 B2 * | 4/2013 | Hair | A61M 3/0262 | 128/200.14 |
| D701,600 S | 3/2014 | Kauffman | | |
| 8,696,648 B2 | 4/2014 | Laerdal et al. | | |
| 8,777,972 B2 | 7/2014 | Burres | | |
| 8,808,317 B2 * | 8/2014 | Braunagel | A61M 3/0262 | 604/540 |
| 8,845,598 B2 * | 9/2014 | Mehta | A61M 3/0241 | 604/256 |
| 8,852,150 B2 * | 10/2014 | Wang | A61M 3/0258 | 604/131 |
| 8,888,752 B2 * | 11/2014 | Cacka | A61M 3/0208 | 604/278 |
| 8,991,660 B2 * | 3/2015 | Hair | B65D 1/32 | 222/211 |
| D757,938 S | 5/2016 | Jackson | | |
| D762,852 S | 8/2016 | Thouement et al. | | |
| 9,884,147 B2 * | 2/2018 | Azeez | A61M 1/0003 | |
| 9,884,148 B2 * | 2/2018 | Mehta | A61M 3/022 | |
| 2002/0010428 A1 * | 1/2002 | Vedrine | A61M 15/0065 | 604/187 |
| 2002/0169422 A1 * | 11/2002 | Ahnblad | A61M 3/0262 | 604/217 |
| 2003/0135228 A1 | 7/2003 | Crespo | | |
| 2003/0158527 A1 * | 8/2003 | Mezzoli | B05B 1/34 | 604/275 |
| 2006/0027603 A1 | 2/2006 | Doyle et al. | | |
| 2006/0253087 A1 * | 11/2006 | Vlodaver | A61M 31/00 | 604/275 |
| 2008/0300527 A1 * | 12/2008 | Bivins | A61F 13/38 | 604/1 |
| 2009/0056709 A1 * | 3/2009 | Worsoff | A61M 31/00 | 128/200.24 |
| 2009/0173650 A1 | 7/2009 | Stein et al. | | |
| 2009/0240239 A1 * | 9/2009 | Yardley | A61F 13/38 | 604/540 |
| 2009/0247941 A1 * | 10/2009 | Lu | A61M 3/0262 | 604/73 |
| 2011/0139149 A1 * | 6/2011 | Cacka | A61M 3/0262 | 128/200.14 |
| 2011/0139824 A1 * | 6/2011 | Cacka | A61M 3/022 | 604/275 |
| 2011/0166523 A1 | 7/2011 | Javer et al. | | |
| 2012/0323221 A1 * | 12/2012 | Gallo | A61M 3/0279 | 604/514 |
| 2013/0184684 A1 | 7/2013 | Yardley | | |
| 2013/0197450 A1 | 8/2013 | Mehta | | |
| 2014/0200507 A1 * | 7/2014 | Azeez | A61M 1/0082 | 604/28 |
| 2015/0039003 A1 * | 2/2015 | Wilson | A61F 13/38 | 606/162 |
| 2016/0030720 A1 * | 2/2016 | Husain | A61K 31/122 | 604/514 |
| 2018/0086545 A1 * | 3/2018 | Gaston | B65D 75/008 | |
| 2018/0256867 A1 * | 9/2018 | Levin | A61M 11/008 | |
| 2019/0184088 A1 * | 6/2019 | Mechor | A61M 3/0279 | |
| 2020/0060877 A1 * | 2/2020 | Belmkaddem | A61F 11/006 | |

* cited by examiner

NASAL CLEANING TOOL

RELATED APPLICATIONS

The present invention is a continuation of and claims the benefit of U.S. Provisional Application No. 62/568,376 filed on Oct. 5, 2017, the entire disclosures of which are incorporated herein by reference.

FIELD OF THE INVENTION

The present invention relates generally to the field of nasal cleaning tools.

BACKGROUND OF THE INVENTION

It is important to maintain clear pathways during a breathing process. Congestion is such pathways can lead to difficulty breathing and not receiving enough oxygen to support bodily functions. The individual who is congested is constantly tired and also has to resort to methods to relieve such congestion.

In instances where the pathway that is congested is in the nasal cavity, often times, removing the congestion requires inserting a tool or object, like a finger, to "scrape" or "pull" away the congestion, which is usually predominantly mucus. Many times, the mucus is partially or fully dried, and with the "scraping" or "pulling" comes the risk of inadvertent nasal cavity lining damage, which can result in bloody discharge and an open wound for infection. As such, a fluid is necessary to rehydrate the dried mucus, but also to deliver a cleansing or moisturizing component. As such, a tool that not only combines a gentler scraping function as well as a fluid delivery device is greatly desired.

Various attempts have been made to solve problems found in nasal cleaning tool art. Among these are found in: U.S. Pat. App. Pub. No. 2011/0166523 to Javer et al.; U.S. Pat. No. 3,635,218 to Ericson; and U.S. Pat. App. Pub. No. 2013/0184684 to Yardley. These prior art references are representative of devices providing such a nasal cleaning tool that also delivers a fluid.

None of the above inventions and patents, taken either singly or in combination, is seen to describe the invention as claimed. Thus, a need exists for a reliable tool, and to avoid the above-mentioned problems.

SUMMARY OF THE INVENTION

The inventor has recognized the aforementioned, inherent problems and lack in the art and observed that there is a need for an A nasal cleaning tool which comprises a deformable reservoir having a volume to hold a plurality of contents inside the reservoir. The deformable reservoir has a bottom section that has a planar surface so that the nasal cleaning tool rests on a horizontal surface. The bottom section is chamfered from a sidewall of the deformable reservoir. The deformable reservoir also has a first section with a continuous intermediate diameter for a majority of the reservoir. A second section has a tapering diameter, an inner diameter of the deformable reservoir generally matches in geometry an outer diameter thereof.

The tool also provides a neck having a continuous inner diameter to enable fluid communication with the deformable reservoir, an outer diameter of the neck tapers downward from the second section of the deformable reservoir; and a scouring portion. The scouring portion has a barrel-shaped hollow tube with a plurality of concentric rings on the exterior surface. The concentric rings are similar in size and shape while a valley is formed when a pair of tapering ends of the concentric adjacent rings meet. The inner diameter of the scouring portion is sized to permit passage of the neck therethrough until the inner diameter of the scouring portion equals the outer diameter of a position on the neck. This provides a friction fit of the scouring portion to the neck, an upper edge of the scouring portion is generally flush with or immediately adjacent to an opening.

The nasal cleaning tool is ideally configured to scrape away mucus from inside a nostril of the nasal cavity while permitting the selective delivery of a fluid from an interior of the nasal cleaning tool.

The nasal cleaning tool may be of unitary in construction and has a deformable material, enabling the user to deform a portion of the tool to forcibly eject a plurality of contents from the interior. The tool may also be deformable in such a way as to allow a user to depress a plurality of sides of the deformable reservoir, thereby forcing the fluid retained therein to travel through the neck and out of the opening at a velocity.

The deformable reservoir may have a generally cylindrically-shape and contain a fluid which may in turn comprise a saline solution. The contents of the nasal cleaning tool may also include a powder. An upper part of the reservoir transitions into the neck which extends away from a center upper part of the deformable reservoir and is in fluid communication the neck. The scouring portion may be attached to the neck or affixed thereto, either by adhesive or mechanical bonding.

The scouring portion may be an integral feature of the neck. An upper and a lower ring may be smaller in diameter than the concentric rings. The ring may comprise a ridge and a pair of opposing tapering ends.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
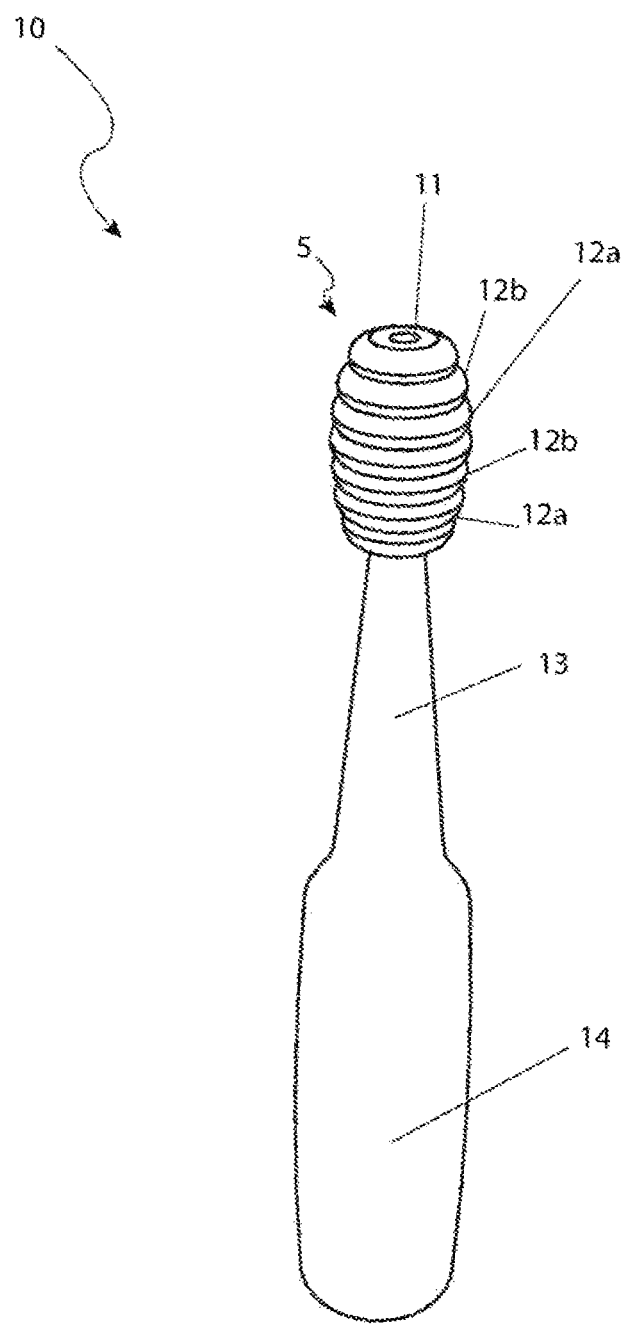
FIG. 1 is a perspective view of a nasal cleaning tool 10, according to an embodiment of the present invention.

DESCRIPTIVE KEY 5 scouring portion
10 nasal cleaning tool
11 opening
12a scouring portion ridge
12b scouring portion valley
13 neck
14 reservoir
15 bottom
20 interior

DESCRIPTION OF THE INVENTION

The present invention is directed to a nasal cleaning tool (herein described as the "tool") 10, that performs the duties of gently scraping away mucus from inside a nostril of the nasal cavity as well as permitting the selective delivery of a fluid from the interior 20 of the tool 10. The tool 10 is preferably unitary in construction and has a deformable material, enabling a user to deform a portion of the tool 10 to forcibly eject the contents from the interior 20.

Figure 2:
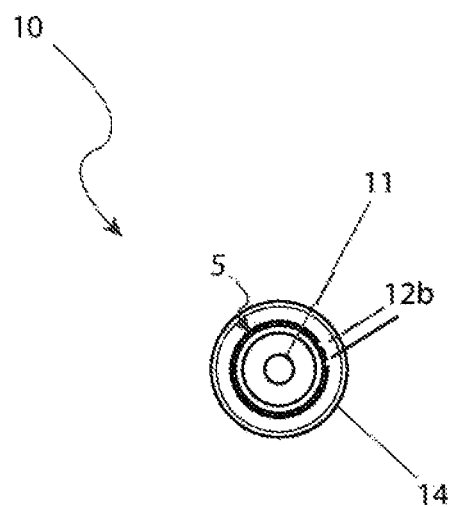
FIG. 2 is a top plan view of the nasal cleaning tool 10, according to an embodiment of the present invention.
Figure 3:
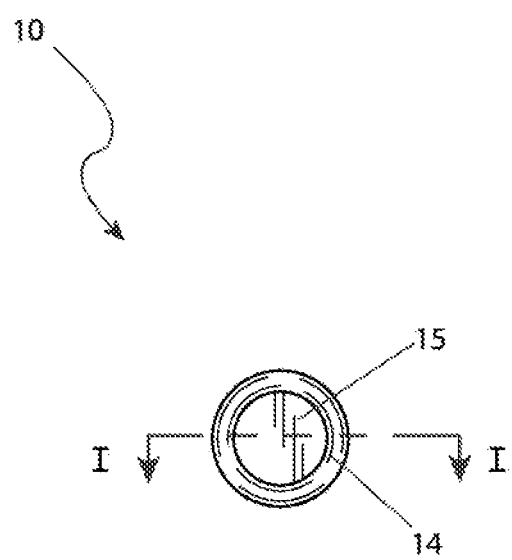
FIG. 3 is a bottom plan view of the nasal cleaning tool 10, according to an embodiment of the present invention.
Figure 4:
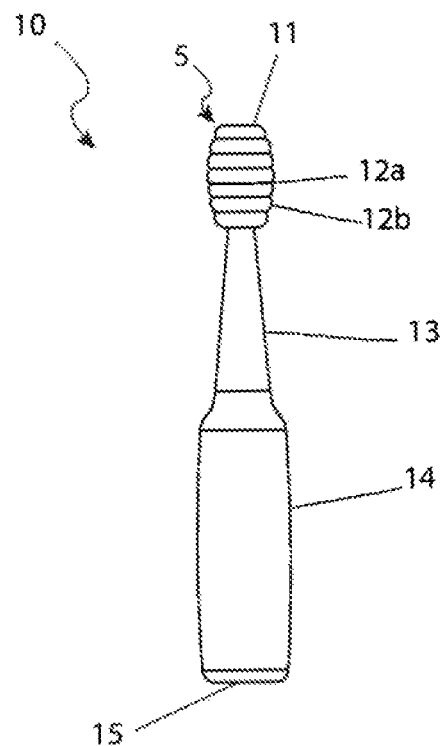
FIG. 4 is a side elevation view of the nasal cleaning tool 10, according to an embodiment of the present invention; and, FIG. 5 is a cross-sectional view of the nasal cleaning tool 10 along the line I-I (please see FIG. 3), according to an embodiment of the present invention.
Figure 5:
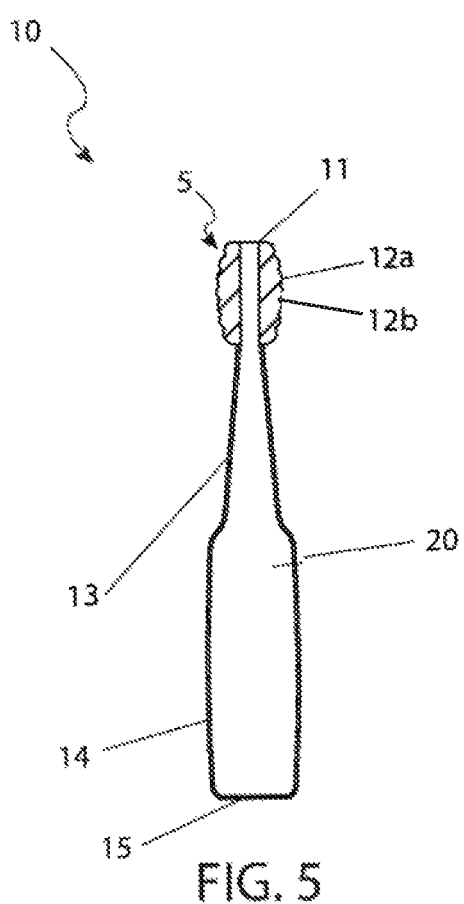

Referring now to the drawings, FIG. 1, shows a perspective view of the tool 10, FIG. 2 shows a top plan view, FIG. 3 shows a bottom plan view, FIG. 4 shows a side elevation view, and FIG. 5 shows a cross-sectional view of the tool 10 along the line 1-1 in FIG. 3. The tool 10 is preferably provided in three (3) distinct parts, a deformable reservoir 14, a neck 13, and a scouring portion 5. The tool 10 is symmetrical with respect to an axial centerline (i.e. vertical centerline when the tool 10 is in an upright position), as well as a radially (i.e. radiating lines from a common center focal point when the tool 10 is in an upright position). The deformable reservoir 14 and the neck 13 are also elongated, as illustrated in FIG. 1.

The deformable reservoir 14 is generally cylindrically-shaped and has a volume to hold contents therein, such as a fluid or a powder. The reservoir 14 has a bottom section 15 that has a planar surface so that the tool 10 can rest on a horizontal surface. The bottom 15 is envisioned to be chamfered from the sidewall of the reservoir 14. An upper part of the reservoir 14 transitions into the neck 13 which extends away from a center upper part of the reservoir 14 and is in fluid communication therewith. The reservoir 14 has a first section with a continuous an intermediate diameter for the majority thereof, and a second section with a tapering diameter (i.e. transitions from larger to smaller). The inner diameter of the reservoir 14 generally matches in geometry the outer diameter thereof. The neck 13 has a continuous inner diameter to enable fluid communication with reservoir 14. The outer diameter of the neck 13 tapers downward (i.e. transitions from larger to smaller) from the second section of the reservoir 14. The reservoir 14 and neck 13 are preferably manufactured out of the same material and provided as a unitary device.

The scouring portion 5 is preferably a harder material than the reservoir 14 and neck 13 and is preferably fashioned as a barrel-shaped hollow tube with a plurality of concentric rings on the exterior surface. The concentric rings are similar in size and shape, or alternately, an upper and a lower ring can be smaller in diameter than the intervening rings. Each ring comprises a ridge 12a and a pair of opposing tapering ends (i.e. transitioning from larger to smaller). A valley 12b is formed when tapering ends of adjacent rings meet. The inner diameter of the scouring portion 5 is sized to permit the passage of the neck 13 therethrough until the inner diameter of the scouring portion 5 equals the outer diameter of a position on the neck 13, thereby providing a friction fit of the scouring portion 5 to the neck 13. Typically, this location is such that the upper edge of the scouring portion 5 is generally flush with or immediately adjacent to the opening 11. When installed, the rings provide a "scouring" or "scrubbing" means when the scouring portion 5 is inserted into a nostril of the nasal cavity and used to dislodge mucus material. It is also appreciated that any other texturized surface or ridges can be present on the outer surface of the scouring portion 5 and thus, is not a limiting part of the invention. The scouring portion 5 can either be removably attached to the neck 13 or affixed thereto, either by adhesive or mechanical bonding. Alternately, the scouring portion 5 can be an integral feature of the neck 13.

The material is deformable to allow a user to depress the sides of the reservoir 14, thereby forcing fluid retained therein to travel through the neck 13 and out of the opening 11 at a velocity. This is particularly helpful when inserted into a nostril of the nasal cavity to deliver the fluid.

The fluid used is preferably a saline solution but could be any type of fluid and is thus not a limiting part of the invention. Is it appreciated that the fluid delivered could "wet" the scouring portion 5 to provide enhanced cleaning and scrubbing methods.

The invention claimed is:

1. A nasal cleaning tool, consisting of:
   an elongated deformable reservoir having a volume to hold a plurality of contents therein, said elongated deformable reservoir having a bottom section that has a planar surface, said elongated deformable reservoir having a first section with a continuous intermediate diameter, and a second section with a tapering diameter, an inner diameter of said elongated deformable reservoir generally matches in geometry to an outer diameter thereof;
   an elongated neck having a continuous inner diameter to enable fluid communication with said elongated deformable reservoir, an outer diameter of said elongated neck tapers downward from said second section of said elongated deformable reservoir; and
   a scouring portion having a barrel-shaped hollow tube with a plurality of horizontal concentric rings on said exterior surface, said inner diameter of said scouring portion is sized to permit passage of said elongated neck therethrough until said inner diameter of said scouring portion equals said outer diameter of a position on said elongated neck, thereby providing a friction fit of said scouring portion to said elongated neck, an upper edge of said scouring portion is flush with or immediately adjacent to an opening, said scouring portion is made of a harder material than said elongated reservoir and said elongated neck;
   wherein said nasal cleaning tool is symmetrical with respect to an axial centerline;
   wherein said nasal cleaning tool permits said selective delivery of a fluid from an interior of said nasal cleaning tool;
   wherein said nasal cleaning tool is unitary in construction and has a deformable material, said nasal cleaning tool is adapted to allow said user to deform a portion of said tool to forcibly eject a plurality of contents from said interior;
   wherein an upper part of said elongated reservoir transitions into said elongated neck which extends away from a center upper part of said elongated deformable reservoir and is in fluid communication therewith;
   wherein each said concentric ring includes a ridge and a pair of opposing tapering ends;
   wherein said nasal cleaning tool is adapted to allow a user to depress a plurality of sides of said elongated deformable reservoir, thereby forcing said fluid retained therein to travel through said elongated neck and out of said opening;
   wherein said scouring portion is removably attached to said elongated neck or affixed thereto by adhesive or mechanical bonding; and
   wherein said contents includes a fluid.

2. The nasal cleaning tool according to claim 1, wherein said contents includes a saline solution.

\* \* \* \* \*